(12) United States Patent
Petter (10) Patent No.: US 12,227,786 B2
(45) Date of Patent: Feb. 18, 2025

(54) TESTER PAPER AND METHODS OF USE THEREOF FOR DETECTING A BACTERIAL INFECTION

(71) Applicant: Linda Marie Petter, Auburn, WA (US)

(72) Inventor: Linda Marie Petter, Auburn, WA (US)

( * ) Notice: Subject to any disclaimer, the term of this patent is extended or adjusted under 35 U.S.C. 154(b) by 803 days.

(21) Appl. No.: 17/338,285

(22) Filed: Jun. 3, 2021

(65) Prior Publication Data

US 2021/0292806 A1    Sep. 23, 2021

Related U.S. Application Data

(62) Division of application No. 16/427,900, filed on May 31, 2019, now Pat. No. 11,053,531.

(51) Int. Cl.
    *C12Q 1/04*    (2006.01)
    *G01N 21/78*   (2006.01)

(52) U.S. Cl.
    CPC .............. *C12Q 1/04* (2013.01); *G01N 21/78* (2013.01)

(58) Field of Classification Search
    CPC ........................... C12Q 1/04–14; G01N 21/74
    See application file for complete search history.

(56) References Cited

U.S. PATENT DOCUMENTS

| | | | |
|---|---|---|---|
| 3,232,710 | A | 2/1966 | Rieckmann et al. |
| 3,718,543 | A | 2/1973 | Lagomarsino |
| 3,802,842 | A | 4/1974 | Lange et al. |
| 4,024,235 | A | 5/1977 | Weetall et al. |
| 4,355,102 | A | 10/1982 | Quash |
| 4,469,735 | A | 9/1984 | Trokhan |
| 5,225,322 | A | 7/1993 | Wolf |
| 5,861,415 | A | 1/1999 | Majeed et al. |
| 5,989,840 | A | 11/1999 | D'Angelo et al. |
| 6,048,533 | A | 4/2000 | Nguyen |
| 6,589,761 | B1 | 7/2003 | Freadman et al. |
| 2002/0115062 | A1 | 8/2002 | Fletcher et al. |
| 2003/0073153 | A1 | 4/2003 | Phillips et al. |
| 2003/0143530 | A1 | 7/2003 | Klepp et al. |
| 2005/0003343 | A1 | 1/2005 | Palese et al. |
| 2006/0116334 | A1 | 6/2006 | Hendrix |
| 2006/0148097 | A1 | 7/2006 | Yamaguchi et al. |
| 2006/0240453 | A1 | 10/2006 | Jacobs et al. |
| 2008/0069727 | A1 | 3/2008 | Yerazunis et al. |
| 2008/0081341 | A1 | 4/2008 | Maher et al. |
| 2008/0199851 | A1 | 8/2008 | Egan et al. |
| 2009/0029453 | A1 | 1/2009 | Lambotte et al. |
| 2009/0162833 | A1 | 6/2009 | Mertens et al. |
| 2009/0311667 | A1 | 12/2009 | Takahashi et al. |
| 2011/0223193 | A1 | 9/2011 | Mercati |
| 2012/0107429 | A1 | 5/2012 | Lee et al. |
| 2014/0322749 | A1 | 10/2014 | Nishinaga et al. |
| 2015/0056606 | A1 | 2/2015 | Petter |

FOREIGN PATENT DOCUMENTS

WO    WO 2008/096343    8/2008

OTHER PUBLICATIONS

Tami O'Connor "How to make goldenrod paper and some activities" https://uwaterloo.ca/chem13-news-magazine/february-2016/activities/how-make-goldenrod-paper-and-some-activities#:~:text=White%20paper%20dipped%20in%20a,remain%20yellow%20as%20it%20dries., 3 pgs, Feb. 2016 (Year: 2016).*
Burrows Paper Corporation, Technical Data Sheet, Grade: CF 20#/500 BL CR W/S, Part No. 700012, exact publication unknown, retrieved on Mar. 27, 2014.
Burrows Paper Corporation, Technical Data Sheet, Grade: CF 25#/500 BL CR W/S, Part No. 700021, exact publication unknown, retrieved on Mar. 27, 2014.
Burrows Paper Corporation, Technical Data Sheet, Grade: CF 30#/500 CR BL W/S, Part No. 700022, exact publication unknown, retrieved on Mar. 27, 2014.
Dennis L. Myers, M.D., "Urine & Saliva pH Test" (2009), retrieved from the internet: http://www.mmpress.info/id66.htm.
Hardcastle, "A study of the curcumin method for boron determination," 102 pages, Master's Theses, Univ. of Richmond (publication date: Jul. 1, 1960).
Macherey-Nagel "Tumeric paper" (2008).
Merriam-Webster, "Ply," 12 pages, accessed 2020 (2020).
Neenah Paper, "Basis Weights," 4 pages (2019).
Rhodium, Making pH Indicators (2009), retrieved from the internet: www.biologyjunction.com/making%20natural%20ph%20indicators.doc.
Whatman, "Qualitative Filter Papers-Standard Grades," 6 pages (2007).

* cited by examiner

*Primary Examiner* — Thane Underdahl
(74) *Attorney, Agent, or Firm* — Perkins Coie LLP (57) ABSTRACT

In various embodiments, the present disclosure provides testers for detecting a bacterial infection and methods of production and uses thereof.

9 Claims, 10 Drawing Sheets

TESTER PAPER AND METHODS OF USE THEREOF FOR DETECTING A BACTERIAL INFECTION

CROSS-REFERENCE TO RELATED APPLICATIONS

This application is a divisional of U.S. patent application Ser. No. 16/427,900 filed May 31, 2019, the content of which is herein incorporated in its entirety.

TECHNICAL FIELD

The present invention relates to a tester paper for providing an early indication of illness, more particularly, the present invention provides an early indication, drug free, self-administered test to determine when an individual may harbor respiratory pathogens that may induce illness.

BACKGROUND

Due to the current cost of health care, there is a growing interest in the development of inexpensive self-administered home tests to determine the need to visit a physician or clinic. Known testing systems usually require laboratory analysis and expensive equipment and are generally unavailable and/or unamenable to home use.

SUMMARY

Methods and materials are provided for use in determining whether a subject has a bacterial infection.

In some aspects, the present disclosure provides methods of determining whether a subject has a bacterial infection. In some embodiments, the methods comprises (1) providing a turmeric-treated paper to the subject, wherein the paper has a one or more of: (a) a basis weight of about 20 to about 30 on a #500 scale; (b) a caliper of about 3 to about 6 (1 ply, mil); (c) an average tensile strength of about 10 to about 20 #/in; (d) a porosity of about 2 to about 4 (8 ply, 100 cc, sec.); (e) a moisture content of about 2% to about 10% by weight of the total paper; (f) a brightness of about 70% to about 90%; and/or (g) a stretch of about 1% to about 5% of the total dimensions of the paper, and (2) contacting the turmeric-treated paper with a respiratory secretion sample from the subject, wherein the turmeric-treated paper changes from a first color to a second color when contacted with the respiratory secretion sample if the subject has the bacterial infection.

In another embodiment, the treated portion changes from a first color to a second color within about 60 seconds after contact with the respiratory secretion sample. In some embodiments, the first color is a yellow hue. In some embodiments, the second color is a red hue.

In another aspect, the present disclosure provides testers for indicating whether a subject has a bacterial infection based on a sample of respiratory section of the subject. In some embodiments, the testers comprise: a paper having a portion comprising turmeric, wherein the paper has a one or more of: (a) a basis weight of about 20 to about 30 on a #500 scale; (b) a caliper of about 3 to about 6 (1 ply, mil); (c) an average tensile strength of about 10 to about 20 #/in; (d) a porosity of about 2 to about 4 (8 ply, 100 cc, sec.); (e) a moisture content of about 2% to about 10% by weight of the total paper; (f) a brightness of about 70% to about 90%; and/or (g) a stretch of about 1% to about 5% of the total dimensions of the paper.

In some embodiments, the paper changes from a first color to a second color when the treated portion is contacted with the sample of the respiratory secretion if the subject has a bacterial infection.

In yet another aspect, the present disclosure provides methods for making a tester that determines whether a subject has a bacterial infection. In some embodiments, the methods comprise combining turmeric and alcohol into a solution; filtering the solution to remove sediment; contacting a filter paper in the solution; removing the filter paper from contact with the solution; and drying the filter paper until the alcohol evaporates to form the tester. In some embodiments, the methods further comprise adding a scented compound to the solution. In one embodiment, the methods further comprise affixing the tester to a second substrate.

In another embodiment, the tester is paper. In yet another embodiment, the paper is tissue paper. In some embodiments, the paper is filter paper.

In some embodiments, the average tensile strength is an average of a machine direction and cross direction tensile strength. In some embodiments, the paper has a machine direction tensile strength is about 10 to about 15 #/in. In another embodiment, the paper has a cross direction tensile strength is about 2 to about 5 #/in. In yet another embodiment, the paper has a wet tensile strength of about 1 to about 4 #/in.

DETAILED DESCRIPTION

The present disclosure relates to testers for detecting bacterial infections. For example, testers composed of paper and treated with a color indicator that can provide a rapid detection of a bacterial infection from a respiratory secretion of a subject.

After reading this description it will become apparent to one skilled in the art how to implement the invention in various alternative embodiments and alternative applications. However, all the various embodiments of the present invention will not be described herein. It will be understood that the embodiments presented here are presented by way of example only, and not limitation. As such, this detailed description of various alternative embodiments should not be construed to limit the scope or breadth of the present invention as set forth below.

The detailed description is divided into various sections only for the reader's convenience and disclosure found in any section may be combined with that in another section. Titles or subtitles may be used in the specification for the convenience of a reader, which are not intended to influence the scope of the present disclosure.

Unless the context indicates otherwise, it is specifically intended that the various features of the invention described herein can be used in any combination. Moreover, the disclosure also contemplates that in some embodiments any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Definitions

All numerical designations, e.g., temperature, time, concentration, and a specific paper property, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

It must be noted that as used herein and in the appended claims, the singular forms "a," "an," and "the" include plural referents unless the context clearly dictates otherwise. Thus, for example, reference to "a tester paper" includes a plurality of tester papers.

As used herein the following terms have the following meanings:

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The terms tester, tester paper, filter paper, and paper can be used interchangeably throughout.

Tester

Aspects of the disclosure provide a tester for use in determining whether a subject has a bacterial infection.

In some embodiments, the tester is composed of paper. In some embodiments, the tester is composed of filter paper. In some embodiments, the tester is composed of white paper. In another embodiment, the tester is composed of white filter paper.

Figure 1:
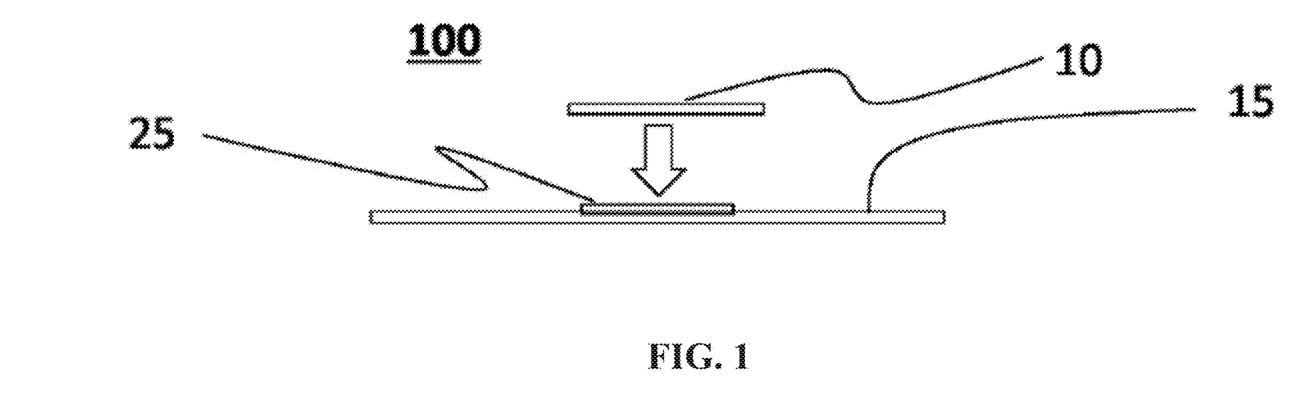
FIG. 1 shows a diagram of an exemplary embodiment of a tester paper in accordance with the present disclosure.
Figure 2:
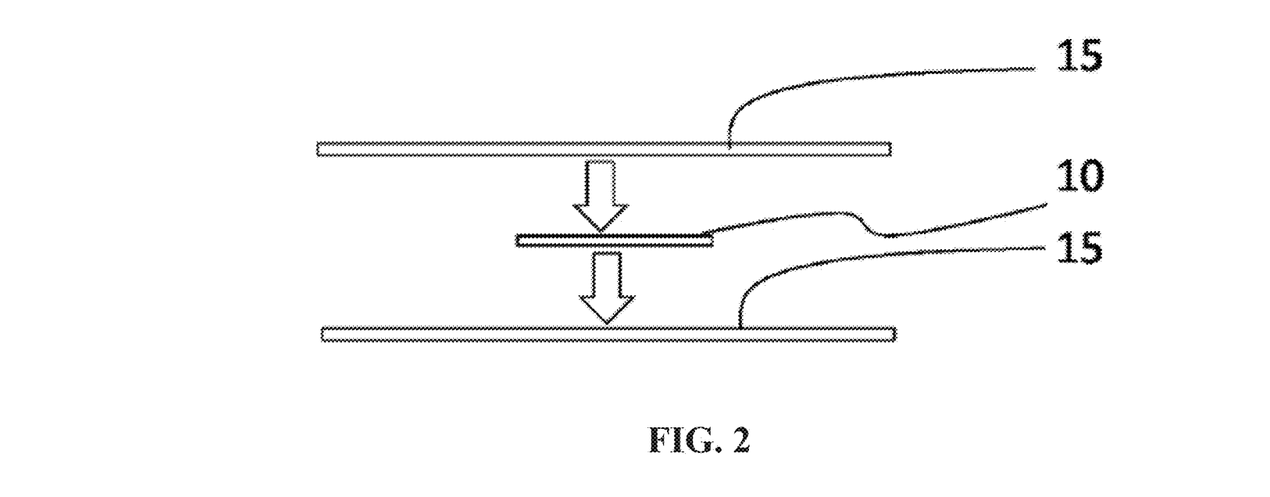
FIG. 2 shows a diagram of an exemplary embodiment of a tester paper in accordance with the present disclosure.

FIG. 1 shows a diagram of an example embodiment of a tester in accordance with the present disclosure labeled 100. In this exemplary embodiment, the tester 100 includes a tester paper 10 treated with a color changing indicator (e.g., turmeric). The tester paper 10 is affixed to a sheet of single ply or multi-ply tissue paper 15 by means of a fixative 25. In one embodiment, the fixative comprises any convenient adhesive as is well known in the paper making industry. FIG. 2 shows a diagram of another example embodiment of a tester in accordance the present disclosure labeled 200. In this exemplary embodiment, the tester 200 includes a tester paper 10 treated with a color changing indicator (e.g., turmeric). The tester paper 10 is affixed between two sheets of single ply or multi-ply tissue paper 15 by means of a fixative. In some embodiments, the size of the tester paper is small enough to allow the opposing sheets of the tissue paper 15 to bind to each other by means of a fixative, thereby holding the tester paper 10 in place. Non-limiting examples of fixatives include glue, paste, or tape. In another embodiment, the fixative comprises a hook and loop material, threading, and/or embossing onto the tissue paper. In one embodiment, when the tester 100 is assembled, the tester appears as a substantially flat, textured sheet of tissue paper to the user.

In some embodiments, the tester paper is a rectangle and/or square having dimensions of about 6 cm by 6 cm, about 12 cm by about 10 cm, about 5 cm by about 10 cm, about 4 cm by about 6 cm, about 3 cm by about 2 cm, about 8 cm by about 8 cm, about 9 cm by about 12 cm, about 10 cm by 10 cm, or about 3 cm by about 10 cm.

In some embodiments, the tester paper is affixed to a second substrate. In another embodiment, the tester paper is affixed between a second and a third substrate. In some embodiments, the second and/or third substrate can prevent unwanted contact with the tester paper such as contact with hands, moisture, oils, or other external influences that may alter the tester paper. In some embodiments, the second substrate or the third substrate is a paper such as tissue paper or a polymeric material that conforms to the tester paper. In some embodiments, the second substrate or the third substrate has a larger area than the tester paper. In some embodiments, the second substrate is a rectangle and/or square having dimensions of about 12 cm by 12 cm, about 8 cm by about 9 cm, about 6 cm by about 10 cm, about 4 cm by about 6 cm, about 6 cm by about 12 cm, about 8 cm by about 8 cm, about 9 cm by about 12 cm, about 10 cm to about 10 cm, or about 5 cm by about 10 cm.

In some embodiments, the tester paper comprises only the treated paper (e.g., does not include a second and/or a third substrate). For example, after the paper is treated, dried, and/or cut, the paper can be used directly for detecting a bacterial infection.

In some embodiments, the tester is designed for facile secretion of the respiratory secretion onto the tester by a subject. For example, in some embodiments, the tester is of a hand-held size such as a standard size of a tissue paper having dimensions of about 10 cm by about 10 cm. In another embodiment, the tester is thin and/or flexible as to easily conform to the nose and/or mouth area of the subject. In yet another embodiment, the tester is soft (i.e., does not have a harsh texture) so as to not irritate the skin of the subject when the tester is placed into contact with the subject's face.

There are several properties of the paper that provide a functional tester paper operable for detecting a bacterial infection. Non-limiting examples of these properties include paper weight, caliper, tensile strength (e.g., machine direction (MD), cross direction (CD), and wet tensile strength), porosity, moisture content, brightness, and stretch.

The basis weight of paper is the weight per unit area. The basis weight is expressed as the number of pounds (lbs) for every 500 sheets of paper. There are number of areas used for calculating basis weight, for example, basis weights can be derived from a standardized unit of paper having a size of 24 inches by 36 inches (2 feet×3 feet). For example, if the paper has a basis weight of 30, this means that 500 sheets of the paper weighs 30 lbs. This standardized unit is referred to as a #500 scale. In some embodiments the tester paper has a basis weight of about 10, about 12, about 14, about 16, about 18, about 20, about 22, about 24, about 26, about 28, about 30, about 32, about 34, about 36, about 38, about 40, about 42, about 44, about 46, about 48, or about 50 on a #500 scale. In some embodiments, the tester paper has a basis weight of about 10 to about 15, about 20 to about 30, about 30 to about 40, about 25 to about 35, about 25 to about 30, about 35 to about 40, about 20 to about 40, or about 15 to about 40 on a #500 scale.

Paper caliper refers to the thickness of a single sheet of paper. The caliper of the tester paper effects various parameters such as tensile strength, moisture content, and/or paper stretch. The caliper of paper is measured in thousandths of an inch (mils) of a ply of paper (1 ply, mil). In some embodiments, the tester paper has a caliper of about 2 (1 ply, mil), about 2.2 (1 ply, mil), about 2.4 (1 ply, mil), about 2.6 (1 ply, mil), about 2.8 (1 ply, mil), about 3 (1 ply, mil), about 3.2 (1 ply, mil), about 3.4 (1 ply, mil), about 3.6 (1 ply, mil), about 3.8 (1 ply, mil), about 4 (1 ply, mil), about 4.2 (1 ply, mil), about 4.4 (1 ply, mil), about 4.6 (1 ply, mil), about 4.8 (1 ply, mil), about 5 (1 ply, mil), about 5.2 (1 ply, mil), about 5.4 (1 ply, mil), about 5.6 (1 ply, mil), about 5.8 (1 ply, mil), about 6 (1 ply, mil), about 6.2 (1 ply, mil), about 6.4 (1 ply, mil), about 6.6 (1 ply, mil), about 6.8 (1 ply, mil), or about 7 (1 ply, mil). In some embodiments, the tester paper has a caliper of about 3 to about 6 (1 ply, mil), about 5 to about 6 (1 ply, mil), about 5.2 to about 6.2 (1 ply, mil), about 4 to about 5.6 (1 ply, mil), about 5 to about 5.5 (1 ply, mil), about 2 to about 6 (1 ply, mil), about 3 to about 5 (1 ply, mil), about 2.5 to about 4 (1 ply, mil), or about 2.6 to about 5.5 (1 ply, mil).

Tensile strength refers to the maximum amount of force that a sheet of paper can support without breaking (e.g., tearing). Tensile strength is measured as the force per unit width of a sheet of paper. Non-limiting examples as ways to express tensile strength include pounds per lineal inch (PLI), newtons per meter (N/m), and/or pounds per inch width. In some embodiments, the tensile strength is expressed as a number (#) per inch width of the paper (#/in), where number can refer to parameters such as weight, force, or sheets of paper. Tensile strength is indicative of fiber strength, fiber bonding and fiber length. The tensile strength of a sheet of paper is different based on fiber direction. This is because the fiber orientation is dissimilar between machine direction (MD) and cross direction (CD), and as such, the tensile strength is measured in both directions. MD is the direction of the paper sheet which is running on the machine whereas CD means the direction, which is perpendicular to the paper sheet that is running on the machine during paper making. In some embodiments the tester paper has a MD tensile strength of about 6 #/in, about 8 #/in, about 10 #/in, about 12 #/in, about 14 #/in, about 16 #/in, about 18 #/in, or about 20 #/in. In some embodiments, the tester paper has a MD tensile strength of about 6 to about 14 #/in, about 10 to about 14 #/in, about 12 to about 16 #/in, about 8 to about 12 #/in, or about 6 to about 20 #/in. In some embodiments, the tester paper has a CD tensile strength of about 2 #/in, about 2.5 #/in, about 3 #/in, about 3.5 #/in, about 4 #/in, about 4.5 #/in, about 5 #/in, about 5.5 #/in, about 6 #/in, about 6.5 #/in, about 7 #/in, about 7.5 #/in, or about 8 #/in. In some embodiments, tester paper has a CD tensile strength of about 2 to about 5 #/in, about 2.5 to about 5.5 #/in, about 3 to about 6 #/in, about 2.5 to about 4.5 #/in, about 3.5 to about 4.5 #/in, about 4 to about 5 #/in, about 2 to about 5 #/in, or about 3 to about 8 #/in. In some embodiments, the tester paper has a combined CD and MD tensile strength (i.e., average tensile strength) of about 10 #/in, about 11 #/in, about 12 #/in, about 13 #/n, about 14 #/in, about 15 #/in, about 16 #/in, about 17 #/in, about 18 #/in, about 19 #/in, about 20 #/in, about 21 #/in, about 22 #/in, about 23 #/in, about 24 #/in, or about 25 #/in. In some embodiments, the tester paper has a combined CD and MD tensile strength of about 10 to about 20 #/in, about 15 to about 25 #/in, about 12 to about 17 #/in, about 15 to about 18 #/in, or about 16 to about 18 #/in.

Wet tensile strength refers to the maximum amount of force that a sheet of wet paper can support without break (e.g., tearing). This parameter was considered because, in some embodiments, the tester paper comes into contact with fluid (e.g., respiratory secretion or turmeric-alcohol solution). In some embodiments, the tester paper can withstand tear, rupture, or falling apart when saturated and/or contacted with a fluid. In some embodiments, the tester paper has a wet tensile strength of about 1 #/in, about 1.5 #/in, about 2 #/in, about 2.5 #/in, about 3 #/in, about 3.5 #/in, about 4 #/in, or about 3.5 Min. In some embodiments, the tester paper has a wet tensile strength of about 1 to about 3 #/in, about 2 to about 3.5 #/in, about 2.5 to about 4 #/in, about 2 to about 4 #/in, or about 1 to about 4 #/in.

The porosity of the tester paper is an indication of the paper's ability to accept (e.g., absorb) a fluid (e.g., respiratory secretion). Paper porosity of the present disclosure is expressed as the number of seconds for air to pass through 8 plys of paper in units of seconds/100 cubic centimeters (8 ply, 100 cc, sec.). In some embodiments, the tester paper has a porosity of about 1 (8 ply, 100 cc, sec.), about 1.5 (8 ply, 100 cc, sec.), about 2 (8 ply, 100 cc, sec.), about 2.5 (8 ply, 100 cc, sec.), about 3 (8 ply, 100 cc, sec.), about 3.5 (8 ply, 100 cc, sec.), about 4 8 ply, 100 cc, sec., or about 3.5 (8 ply, 100 cc, sec.). In some embodiments, the tester paper has a porosity of about 1 to about 3 (8 ply, 100 cc, sec.), about 2 to about 3.5 (8 ply, 100 cc, sec.), about 2.5 to about 4 (8 ply, 100 cc, sec.), about 2 to about 4 (8 ply, 100 cc, sec.), or about 1 to about 4 (8 ply, 100 cc, sec.).

Paper comprises a certain percentage of moisture and the physical properties of paper change as result of moisture content. In some embodiments, the tester paper has a volume and/or weight percent of moisture of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% of the total volume and/or weight of the paper. In some embodiments, the tester paper has a volume and/or weight percent of moisture of about 1% to about 10%, about 1% to about 20%, about 2% to about %6, about 5% to about 10%, about 1% to about 5%, about 2% to about 4%, about 5% to about 20%, about 1% to about 15%, about 2% to about 10%, or about 3% to about 6% of the total volume and/or weight of the paper.

The brightness of a sheet of paper is defined as the percentage of reflectance of blue light at a wavelength of 457 nanometers (nm). In one embodiment, the tester paper undergoes a measurable color change in the presence of a respiratory secretion from a subject having a bacterial infection. In some embodiments, the tester paper has a brightness of about 60%, about 65%, about 70%, about 75%, about 80%, about 85%, about 90%, about 95%, or about 100%. In some embodiments, the tester paper has a brightness of about 60% to about 85%, about 80% to about 90%, about 80 to about 85%, about 85% to about 90%, about 75% to about 95%, or about 75% to about 90%.

Paper stretch is the amount of distortion a sheet of paper undergoes under tensile stress. Stretch is expressed as a percent the paper stretches prior to rupturing relative to the total dimensions of the paper. The ability of the paper to stretch and/or conform to the surroundings allows the tester paper to be "user friendly." In some embodiments, the tester paper has a stretch of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% of the total dimensions of the paper. In some embodiments, the tester paper has a stretch of about 1% to about 10%, about 1% to about 20%, about 2% to about 6%, about 5% to about 10%, about 1% to about 5%, about 2% to about 4%, about 5% to about 20%, about 1% to about 15%, about 2% to about 10%, or about 3% to about 6% of the total dimensions of the tester paper.

In some embodiments, the tester is for indicating whether a subject has a bacterial infection based on a sample of respiratory section of the subject. In some embodiments, the tester comprises a paper having one or more of: (a) a basis weight of about 20 to about 30 on a #500 scale; (b) a caliper of about 3 to about 6 (1 ply, mil); (c) an average tensile strength of about 10 to about 20 #/in; (d) a porosity of about 2 to about 4 (8 ply, 100 cc, sec.); (e) a moisture content of about 2% to about 10% by weight and/or volume of the total paper; (f) a brightness of about 70% to about 90%; and/or (g) a stretch of about 1% to about 5% of the total dimensions of the paper. In some embodiments, the paper has a portion treated with turmeric. In some embodiments, the average tensile strength is an average of a MD and CD tensile strength. In some embodiments, the paper has a MD tensile strength of about 10 to about 15 #/in. In some embodiments, the paper has a CD tensile strength of about 2 to about 5 #/in. In some embodiments, the paper has a wet tensile strength of about 1 to about 4 #/in.

In some embodiments, the tester is for indicating whether a subject has a bacterial infection based on a sample of respiratory section of the subject. In some embodiments, the tester comprises a paper having one or more of: (a) a basis weight of about 30 on a #500 scale; (b) a caliper of about 5 (1 ply, mil); (c) a porosity of about 2.5 (8 ply, 100 cc, sec.); (d) a MD tensile strength of about 12 #/in; (e) a CV tensile strength of about 4.5 #/in; (f) a brightness of about 85%; (g) a moisture content of about 4% of the total volume and/or weight of the filter paper; and/or (h) a stretch of about 2% of the total dimensions of the paper.

In another embodiment, the tester comprises a tissue paper treated with a solution of turmeric and alcohol. In yet another embodiment, at least a portion of the tester paper is treated with a solution of turmeric and alcohol. In some embodiments, the paper has been treated by spraying the paper with the turmeric-alcohol solution, soaking the paper in the turmeric-alcohol solution, spattering the paper with the turmeric-alcohol solution, and/or diffusing into the paper the turmeric-alcohol solution.

Methods of Manufacturing Testers for the Detection of Bacterial Infections

The present disclosure also provides methods of making an early indication, drug free, self-administered tester paper for use in determining whether an individual may have a bacterial infection. Non-limiting examples of bacterial infections include whooping cough, strep throat, ear infection, and/or urinary tract infection.

Figure 3:
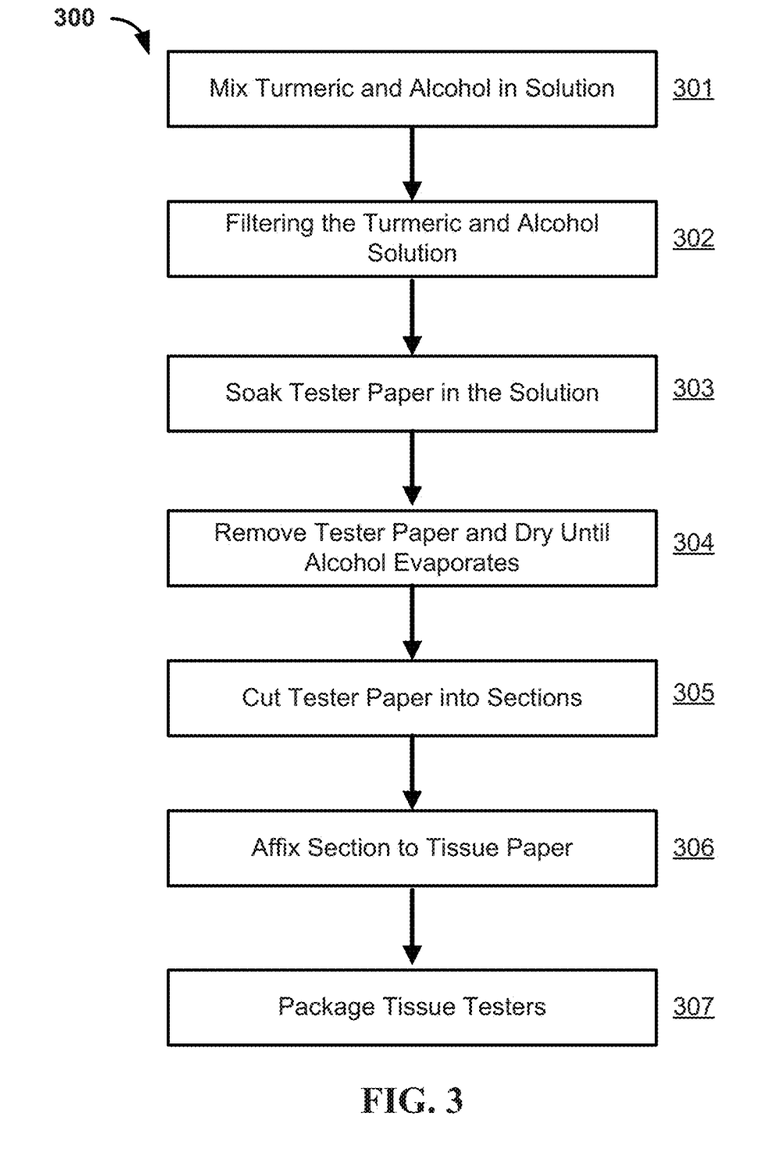
FIG. 3 shows a schematic for an exemplary embodiment for the fabrication of a tester paper in accordance with the present disclosure.

FIG. 3 shows a schematic of an exemplary embodiment of a method, labeled 300, for fabricating a tester in accordance with the present disclosure. The exemplary method 300 includes a process 301 of mixing turmeric and alcohol into a solution. After mixing the turmeric-alcohol solution, the method includes a process 302 in which the turmeric-alcohol solution is filtered to remove undissolved sediment (e.g., undissolved turmeric or dust). The filtration step reduces undissolved sediment that becomes powder residue on the tester paper. This powder could then be inhaled into the lungs of the subject using the tester paper and could cause and/or increase the symptoms of asthma or chronic obstructive pulmonary disease (COPD). The filtration step also helps to remove odors from the tester paper. Following filtration, the method 300 includes a process 303 in which the tester paper is soaked in the filtered turmeric-alcohol solution. In a process 304, the tester paper is removed from the filtered turmeric-alcohol solution and dried until the alcohol evaporates. The method 300 additionally includes a process 305 in which the tester paper is cut into smaller sections. The cut tester papers are then optionally affixed to a tissue paper in a process 306 to form a tissue tester. Lastly, the method 300 includes a process 307 where the tissue testers are packaged and prepared for distribution. In some embodiments, the method 300 can further comprise adding a fragrance into the turmeric-alcohol solution. For example, a mint, orange, lemon, grape, or lavender fragrance.

In some implementations, the method of fabricating the tester for determining whether a subject has a bacterial infection comprises, combining turmeric and alcohol into a solution. In some embodiments the volume ratio of turmeric to alcohol is about 1 to about 5, about 1 to about 10, about 1 to about 20, or about 1 to about 30. In some embodiments, about 10 mL, about 15 mL, about 20 mL, about 25 mL, about 30 mL, about 35 mL, or about 4 mL of turmeric is added to the solution. In another embodiment, about 100 mL, about 150 mL, about 200 mL, about 250 mL, 270 mL, or about 300 mL of alcohol is added to the solution.

In some implementations, the alcohol can be any organic compound having a hydroxyl functional group (e.g., —OH). Non-limiting examples of alcohols include ethanol, methanol, propanol, butanol, or pentanol. In some implementations, the alcohol is rubbing alcohol.

In some implementations, the turmeric can be in various forms. Non-limiting examples of forms of turmeric include raw turmeric, ground turmeric powder, a turmeric oil, or a turmeric paste. In some implementations, the turmeric comprises curcuminoids. Non-limiting examples of curcuminoids include curcumin, demethoxycurcumin and bisdemethoxycurcumin.

In some implementations, the method of fabricating the tester for determining whether a subject has bacterial infection comprises, contacting the tester paper with the turmeric-alcohol solution for at least about 10 seconds, at least about 15 seconds, at least about 20 seconds, at least about 25 seconds, at least about 30 seconds, at least about 35 seconds, at least about 40 seconds, at least about 45 seconds, at least about 50 seconds, at least about 55 seconds, or at least about 60 seconds. In some implementations, a fragrance is added to the turmeric-alcohol solution before the tester paper and solution come in contact. In some implementations, contacting the tester paper with the turmeric-alcohol solution comprises soaking the tester paper in the solution and removing the tester paper from the solution.

In some implementations, the method of fabricating the tester for determining whether a subject has bacterial infection, comprises filtering the turmeric-alcohol solution to remove residual, undissolved material. The residual undissolved material can include sediment for example, dust or other particles in the air introduced during the mixing of the turmeric-alcohol or undissolved turmeric. In some implementations, the filtration step prevents the subject from inhaling residual, undissolved material that would have otherwise remained on the tester paper without the filtration step. In some implementations, the filtration step prevents the subject from inhaling deleterious sediments from the environment and/or undissolved turmeric that may cause and/or increase the symptoms of respiratory disease or conditions. In some embodiments, the filtration step also helps to improve the odor of the tester by removing exogenous sediment that can cause an unsatisfactory smell.

In some implementations, the method of fabricating the tester comprises, affixing the tester paper to a tissue paper with a fixative such as glue, paste, and/or tape. In yet another embodiment, the tester paper is affixed to the tissue paper with a fixative such as a hook and loop material, threading, and/or embossing onto the tissue paper. In some embodiments, the tester paper is not affixed to a tissue paper and is used directly after treating, drying, and/or cutting.

In some implementations, the method of fabricating the tester for determining whether a subject has a bacterial infection, comprises combining turmeric and alcohol into a solution, filtering the solution to remove sediment, contacting a filter paper with the solution, and removing the filter paper from contact with the solution, and drying the filter paper until the alcohol evaporates to form the tester. In some embodiments, the method further comprises cutting the filter paper into smaller pieces and affixing them to a tissue paper. In some implementations, the contacting step comprises soaking the filter paper in the solution and removing the filter paper from the solution.

In some implementations, the method of fabricating the tester for determining whether the subject has a bacterial infection, comprises combining turmeric and alcohol into a solution, filtering the solution to remove sediment, and contacting a filter paper having one or more of: (a) a basis weight of about 20 to about 30 on a #500 scale; (b) a caliper of about 3 to about 6 (1 ply, mil); (c) an average tensile strength of about 10 to about 20 #/in; (d) a porosity of about 2 to about 4 (8 ply, 100 cc, sec.); (e) a moisture content of about 2% to about 10% by weight and/or volume of the total paper; (f) a brightness of about 70% to about 90%; and/or (g) a stretch of about 1% to about 5% of the total dimensions of the paper with the solution. In some implementations, the method further comprises removing the filter paper from contact with the solution and drying the filter paper until the alcohol evaporates to form the tester. In some implementations, the contacting step comprises soaking the filter paper in the solution and removing the filter paper from the solution. In some implementations, the average tensile strength is an average of a MD and CD tensile strength. In some implementations, the paper has a MD tensile strength of about 10 to about 15 #/in. In some implementations, paper has a CD tensile strength of about 2 to about 5 #/in. In some implementations, the tester paper has a wet tensile strength of about 1 to about 4 #/in.

In yet another implementation, the method of fabricating the tester for determining if the subject has a bacterial infection, comprises combining turmeric and alcohol into a solution, filtering the solution to remove sediment, contacting a filter paper having one or more of: (a) a basis weight of about 30 on a #500 scale; (b) a caliper of about 5 (1 ply, mil); (c) a porosity of about 2.5 (8 ply, 100 cc, sec.); (d) a MD tensile strength of about 12 #/in; (e) a CV tensile strength of about 4.5 #/in; (f) a brightness of about 85%; (g) a moisture content of about 4% of the total volume and/or weight of the filter paper; and/or (h) a stretch of about 2% of the total dimensions of the filter paper with the solution. In some implementations, the method further comprises removing the filter paper from contact with the solution and drying the filter paper until the alcohol evaporates to form the tester. In some implementations, the contacting step comprises soaking the filter paper in the solution and removing the filter paper from the solution.

Methods of Detecting Bacterial Infections

Also provided are methods of using the tester to determine whether a subject has a bacterial infection.

Figure 4:
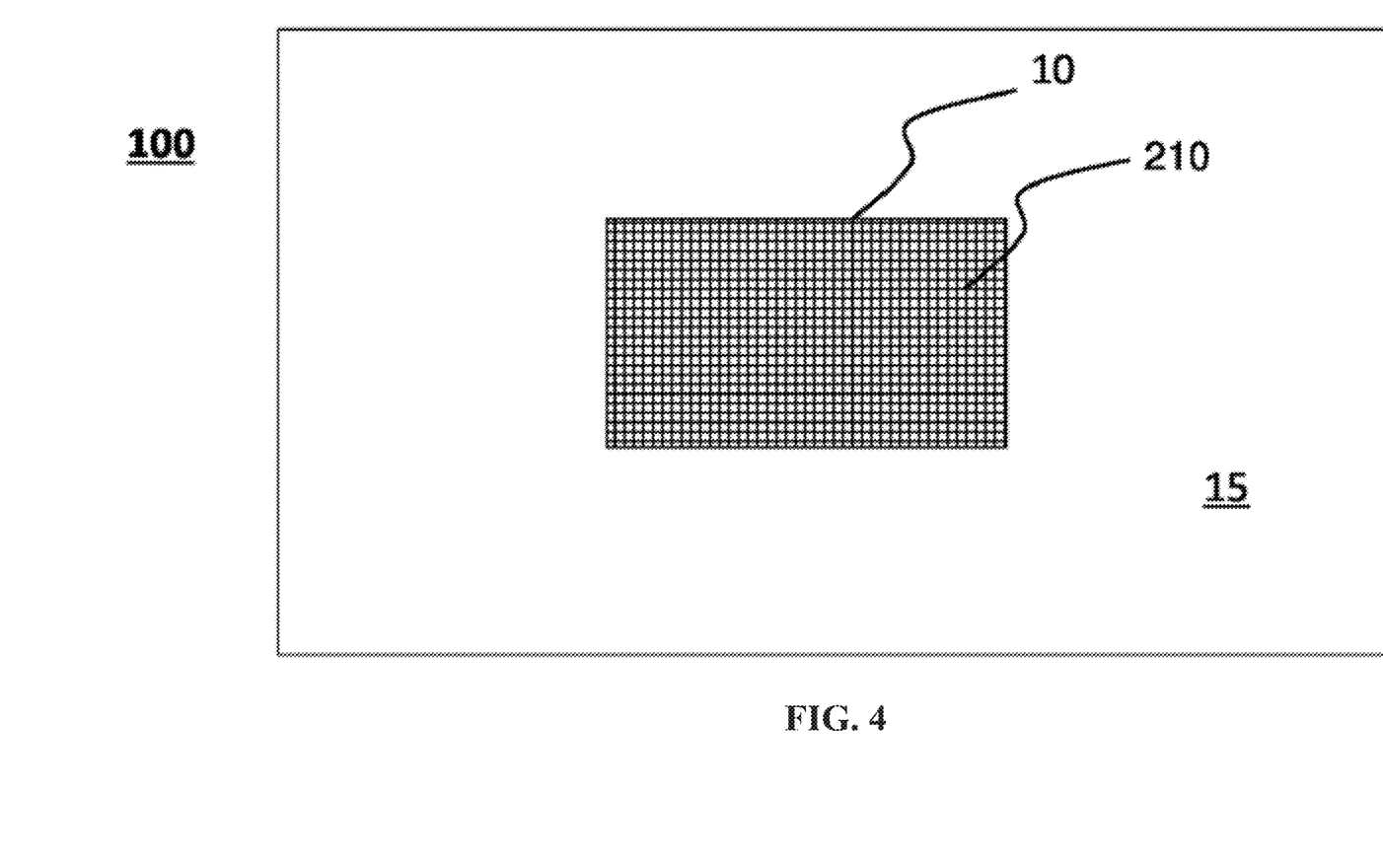
FIG. 4 shows a diagram of an exemplary embodiment of a tester paper indicating the presence of a bacterial infection in accordance with the present disclosure.

FIG. 4 shows an example embodiment of a tester in accordance with the present disclosure labeled 100 indicating the presence of an illness after exposure to a respiratory secretion. In this exemplary embodiment, the tester 100 comprises a tester paper 10 placed on top of a tissue paper 15. The gridded pattern 210 signifies a color change (e.g., as opposed to a non-gridded pattern indicating no color change) from yellow to red/brown. The observation of the color change indicates either to the subject or to a doctor the presence of a bacterial infection. In another embodiment, the tester does not include the tissue paper 15 and is composed only of the tester paper 10. In some embodiments, the tester paper serves as the entire tester.

In various embodiments, the disclosure provides methods of determining whether a subject has a bacterial infection. In some embodiments, the methods comprise (a) providing a turmeric-treated paper to the subject, wherein the turmeric-treated paper has one or more of: a basis weight of about 20 to about 30 on a #500 scale; a caliper of about 3 to about 6

(1 ply, mil); an average tensile strength of about 10 to about 20 #/in; a porosity of about 2 to about 4 (8 ply, 100 cc, sec.); a moisture content of about 2% to about 10% by weight and/or volume of the total paper; a brightness of about 70% to about 90%; and/or a stretch of about 1% to about 5% of the total dimensions of the paper and (b) contacting the turmeric-treated paper with a respiratory secretion sample, wherein the turmeric-treated paper changes from a first color to a second color when contacted with the respiratory secretion sample if the subject has the bacterial infection. In some embodiments, if the subject is determined to have a bacterial infection, the subject is prescribed a drug (e.g., an antibacterial agent) to treat the bacterial infection. In some embodiments, the average tensile strength is an average of a MD and CD tensile strength. In some embodiments, the paper has a MD tensile strength of about 10 to about 15 #/in. In some embodiments, the paper has a CD tensile strength of about 2 to about 5 #/in. In some embodiments, the paper has a wet tensile strength of about 1 to about 4 #/in.

In some embodiments, the disclosure provides methods of determining whether a subject has a bacterial infection. In another embodiment, the methods comprises (a) providing a turmeric-treated paper to the subject, wherein the turmeric-treated paper has one or more of: a basis weight of about 30 on a #500 scale; a caliper of about 5 (1 ply, mil); a porosity of about 2.5 (8 ply, 100 cc, sec.); a MD tensile of about 12 #/in; a CV tensile of about 4.5 #/in; a brightness of about 85%; a moisture content of about 4% of the total volume and/or weight of the filter paper, and/or a stretch of about 2% and (b) contacting the turmeric-treated paper with a respiratory secretion sample from the subject, wherein the turmeric-treated paper changes from a first color to a second color when contacted with the respiratory secretion sample if the subject has the bacterial infection. In some embodiments, if the subject is determined to have a bacterial infection, the subject is prescribed a drug (e.g., an antibacterial agent) to treat the bacterial infection.

In some embodiments, the first color of the paper is yellow and if the paper does not change color upon contact with a respiratory secretion, the subject who provided the respiratory secretion is determined to not have a bacterial infection. In some embodiments, the subject is not retested.

In another embodiment, the first color of the paper is yellow, and the second color of the paper is tan. If upon contact with a respiratory secretion, the paper turns tan and does not become red/brown, the subject who provided the respiratory secretion could, over time, progress to a bacterial infection and/or recover from a potential bacterial infection. If the paper turns from yellow to tan, the subject is retested within a few days (e.g., 1, 2, 3, or more) to determine if the subject has progressed to a bacterial infection and/or has recovered from a potential bacterial infection.

In another embodiment, the first color of the paper is yellow, and the second color of the paper is red/brown. If upon contact with a respiratory secretion, the paper turns red/brown, the subject who provided the respiratory secretion is determined has having a bacterial infection. In some embodiments, the subject is counseled to schedule an appointment with a doctor to receive antibiotic treatment. In some embodiments, the subject is not retested.

In some embodiments, the methods provide an instantaneous or near instantaneous detection of a bacterial infection where the tester paper rapidly changes from a first color to a second color when contacted with a sample of a respiratory resection. In some embodiments, the treated portion of the paper changes from a first color to a second color in less than about 30 seconds, less than about 35 seconds, less than about 40 seconds, less than about 45 seconds, less than about 50 seconds, less than about 60 seconds, less than about 65 seconds, less than about 70 seconds, less than about 75 seconds, or less than about 80 seconds after contact with the respiratory secretion sample.

In some embodiments, the disclosure provides methods of monitoring whether a subject has a bacterial infection. In another embodiment, the methods comprise (a) providing a turmeric-treated paper to the subject, wherein the turmeric-treated paper has one or more of: a basis weight of about 20 to about 30 on a #500 scale; a caliper of about 3 to about 6 (1 ply, mil); an average tensile strength of about 10 to about 20 #/in; a porosity of about 2 to about 4 (8 ply, 100 cc, sec.); a moisture content of about 2% to about 10% by weight and/or volume of the total paper; a brightness of about 70% to about 90%; and/or a stretch of about 1% to about 5% of the total dimensions of the paper and (b) contacting the turmeric-treated paper with a respiratory secretion sample from the subject, wherein the turmeric-treated paper changes from a first color to a second color when contacted with the respiratory secretion sample if the subject has the bacterial infection. In some embodiments, the subject is administered an antibiotic therapy to treat the bacterial infection and is retested to assess whether the subject has and/or is recovered from the bacterial infection. In some embodiments, the subject is retested multiple times, for example 1, 2, 3, 4, or more times. In some embodiments, the average tensile strength is an average of a MD and CD tensile strength. In some embodiments, the paper has a MD tensile strength of about 10 to about 15 #/in. In some embodiments, the paper has a CD tensile strength of about 2 to about 5 #/in. In some embodiments, the paper has a wet tensile strength of about 1 to about 4 #/in.

In yet another embodiment, the disclosure provides methods of monitoring a subject for a bacterial infection, the methods comprising (a) providing a turmeric-treated paper to the subject, wherein the turmeric-treated paper has one or more of: a basis weight of about 30 on a #500 scale; a caliper of about 5 (1 ply, mil); a porosity of about 2.5 (8 ply, 100 cc, sec.); a MD tensile of about 12 #/in; a CV tensile of about 4.5 #/in; a brightness of about 85%; a moisture content of about 4% of the total volume and/or weight of the filter paper; and/or a stretch of about 2% of the total dimensions of the paper and (b) contacting the turmeric-treated paper with a respiratory secretion sample from the subject, wherein the turmeric-treated paper changes from a first color to a second color when contacted with the respiratory secretion sample if the subject has the bacterial infection. In some embodiments, the subject has previously been determined as having a bacterial infection and is on antibiotic therapy. In some embodiments, the subject is administered an antibiotic therapy to treat the bacterial infection and is retested to assess whether the subject has and/or is recovered from the bacterial infection. In some embodiments, the subject is retested multiple times, for example 1, 2, 3, 4, or more times.

EXAMPLES

Example 1: Efficacy of the Tester Paper in Detecting a Bacterial Infection

The objective of the following study was to determine the efficacy of a tester paper in accordance with the present disclosure for detecting whether a subject has a bacterial infection.

1.1 Tester Paper

Several filter papers were explored in this study to determine the optimal paper with characteristics that enabled a high degree of color retention and that also prevented colors from bleeding. Non-limiting examples of paper characteristics considered included basis weight, caliper, porosity, tensile strength, brightness, and stretch. The characteristics of two the filter papers tested are enumerated below in Tables 1 and 2.

TABLE 1

Characteristics of Filter Paper 1

| Properties | Filter Paper |
| --- | --- |
| Basis Weight (# 500 scale) | 30.0 |
| Caliper (1 ply, mil) | 5.2 |
| Porosity (8 ply, 100 cc, sec) | 2.5 |
| MD Tensile (#/in) | 12.0 |
| CD Tensile (#/in) | 4.5 |
| Wet MD Tensile (#/in) | 2.5 |
| Brightness (%) | 84.0 |
| Moisture (%) | 4.0 |
| Stretch (%) | 2.0 |

TABLE 2

Characteristics of Filter Paper 2

| Properties | Filter Paper |
| --- | --- |
| Basis Weight (# 500 scale) | 25.0 |
| Caliper (1 ply, mil) | 4.5 |
| Porosity (8 ply, 100 cc, sec) | 1.5 |
| MD Tensile (#/in) | 10.0 |
| CD Tensile (#/in) | 3.0 |
| Wet MD Tensile (#/in) | 2.0 |
| Brightness (%) | 84.0 |
| Moisture (%) | 2.0 |
| Stretch (%) | 2.0 |

1.2 Preparation of the Tester

The tester was prepared by mixing 20 mL (i.e., 4 teaspoons) of turmeric with 237 mL (i.e., 1 cup) of rubbing alcohol to form a turmeric-alcohol solution. The turmeric-alcohol solution was then filtered to remove undissolved sediment. White filter paper with the characteristics as defined in Table 1 and Table 2 was then soaked in the solution for approximately 30 seconds or until the paper turned yellow and/or golden in color. The treated paper was then air dried for approximately 24 hours to allow the alcohol to fully evaporate. After drying, the filter paper was cut into small pieces and affixed onto a tissue (e.g., a generic facial tissue). An exemplary flow diagram for the preparation of the tester paper is shown in FIG. 3. A plurality of samples was prepared and tested experimentally to determine their efficacy in detecting a bacterial infection from a respiratory secretion.

1.3 Results

A respiratory secretion was obtained from both the nose and mouth of each study subject. The respiratory secretion was then applied to the tester paper and evaluated based on a color change. The tester paper changed colors within approximately 30 to 60 seconds after an initial contact with the respiratory secretion. The reaction occurred at the initial point of contact and spread outwards (i.e., not in an up down or bottom up manner). The tester papers upon contact with a respiratory secretion are shown in FIGS. 5A and 5B, FIGS. 6A and 6B, and FIGS. 7A-7C.

As shown in FIGS. 5A and 5B, FIGS. 6A and 6B, and FIGS. 7A-7C there were three possible indications (e.g., color changes) upon the contact of the respiratory secretion with the tester paper. Each of these colors correspond to a different clinical indication regarding the subject's health.

Figure 5A:
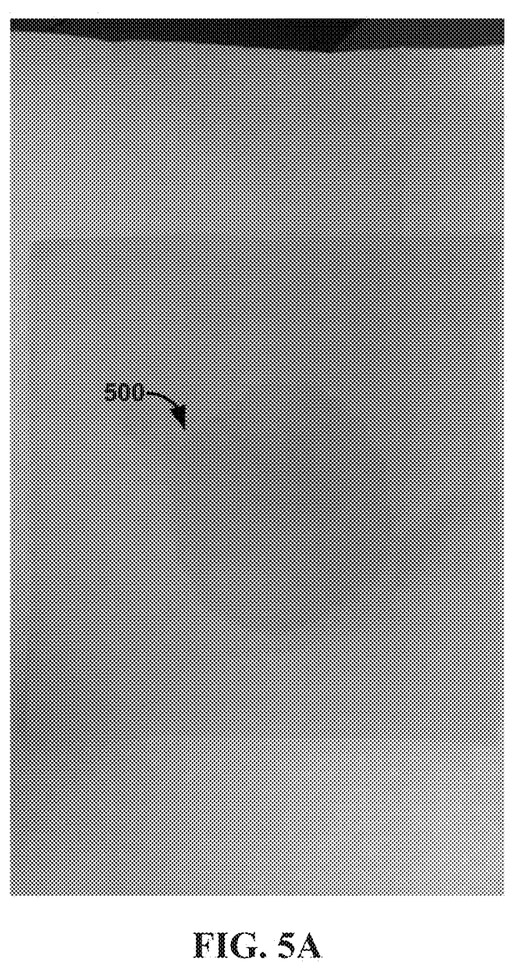
FIGS. 5A and 5B show images of an exemplary embodiment of a tester paper in accordance with the present disclosure indicating the absence of a bacterial infection.
Figure 5B:
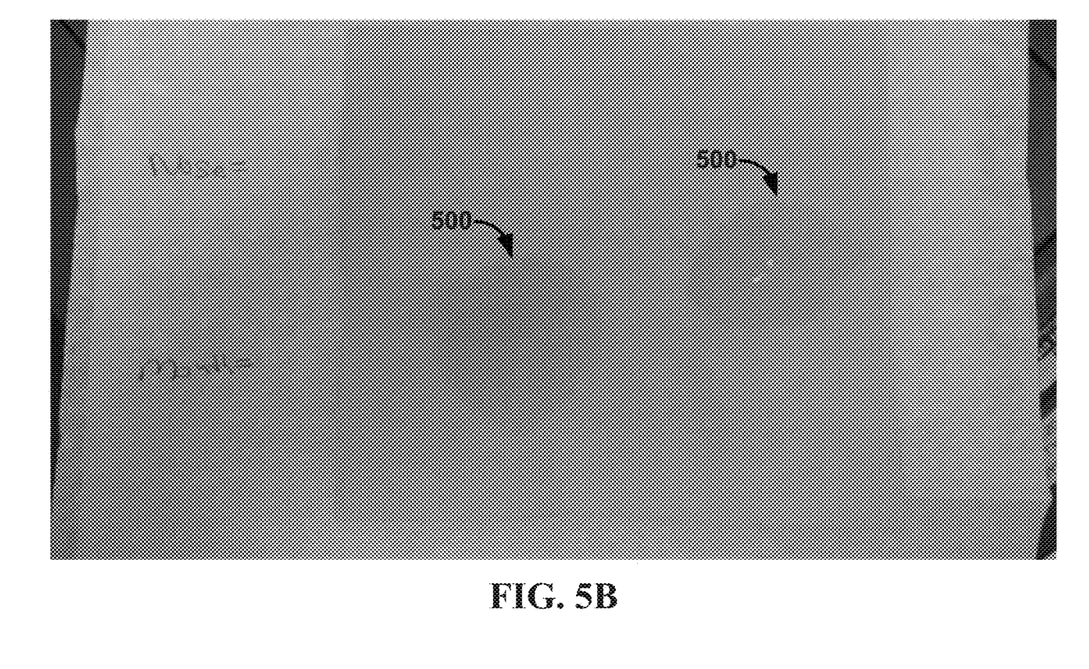

None color change: FIGS. 5A and 5B show that upon contact with the respiratory secretion, the tester paper does not change color (e.g., remained yellow) as denoted by the label 500. Subjects from this test group were determined not to have a bacterial infection. The subjects did not need to be retested to confirm the diagnosis. However, while the subject does not have a bacterial infection, the subject could have a viral infection.

Figure 6A:
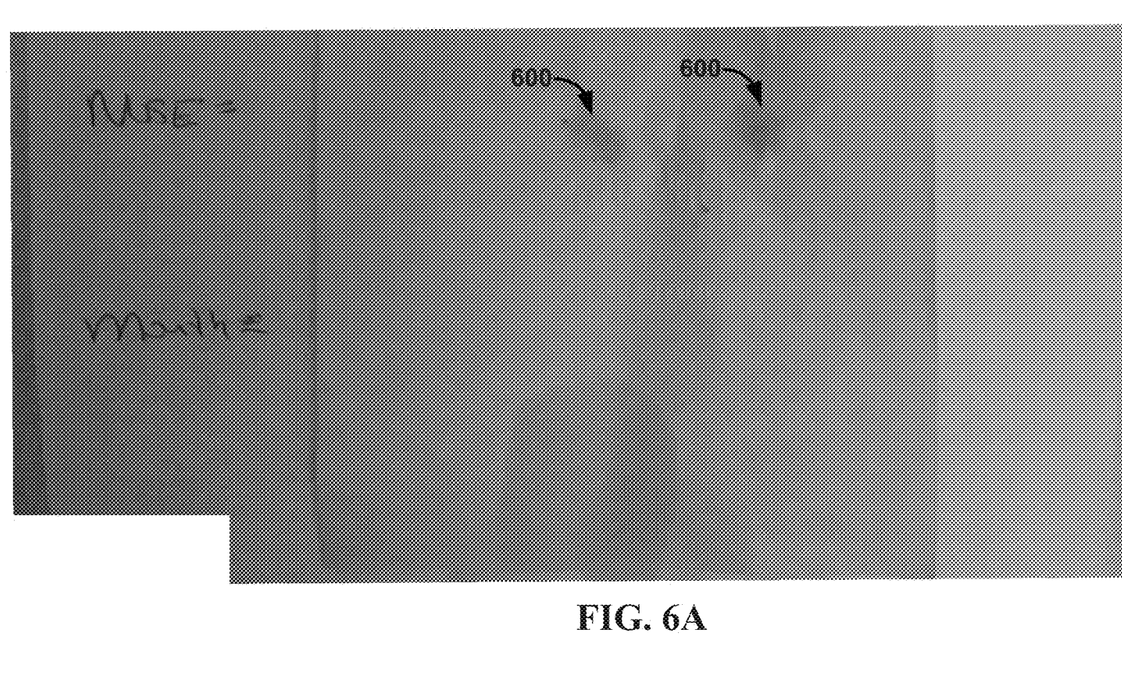
FIGS. 6A and 6B show images of an exemplary embodiment of a tester paper in accordance with the present disclosure indicating the potential presence of a bacterial infection.
Figure 6B:
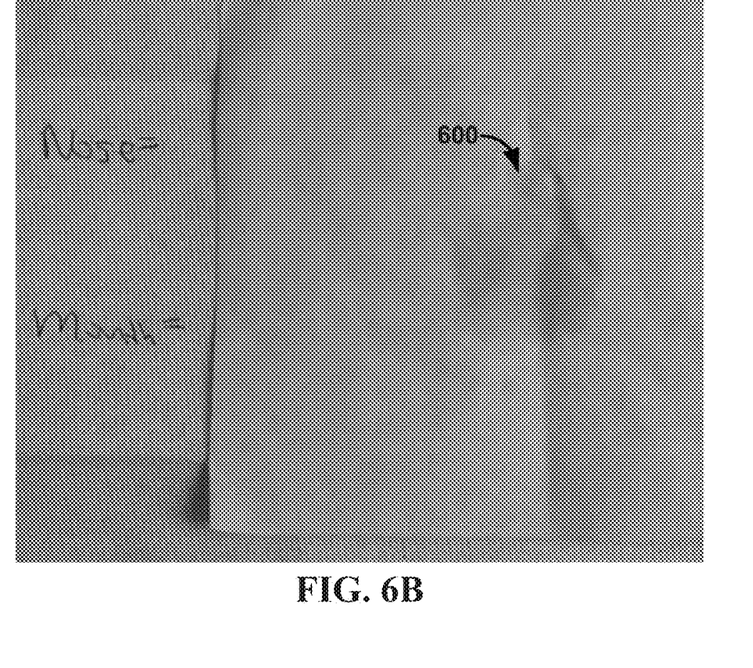

Color change to tan: FIGS. 6A and 6B show that upon contact with the respiratory secretion, the tester paper changed from yellow to tan denoted by the label 600. If the tester paper developed into a tan color but did not become a dark red and/or brown color, this subject was determined not to have a bacterial infection. Note, it could take up to approximately 60 seconds for the tester paper to fully change color. However, this subject could, overtime, progress to a bacterial infection or the subject could recover and/or resolve a potential bacterial infection. Subjects from this tester group, were retested with a tester paper in a few days to follow their progress and to determine if the subject progressed either to a bacterial infection and/or recovered from a potential bacterial infection.

Figure 7A:
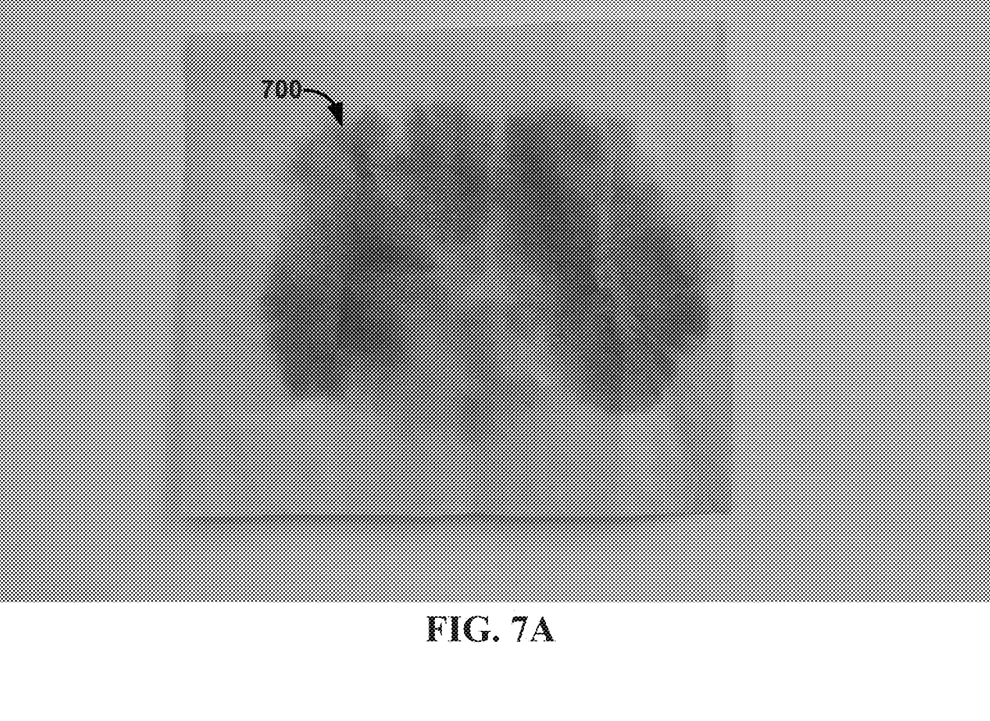
FIGS. 7A-7C show images of an exemplary embodiment of a tester paper in accordance with the present disclosure indicating the presence of a bacterial infection.
Figure 7B:
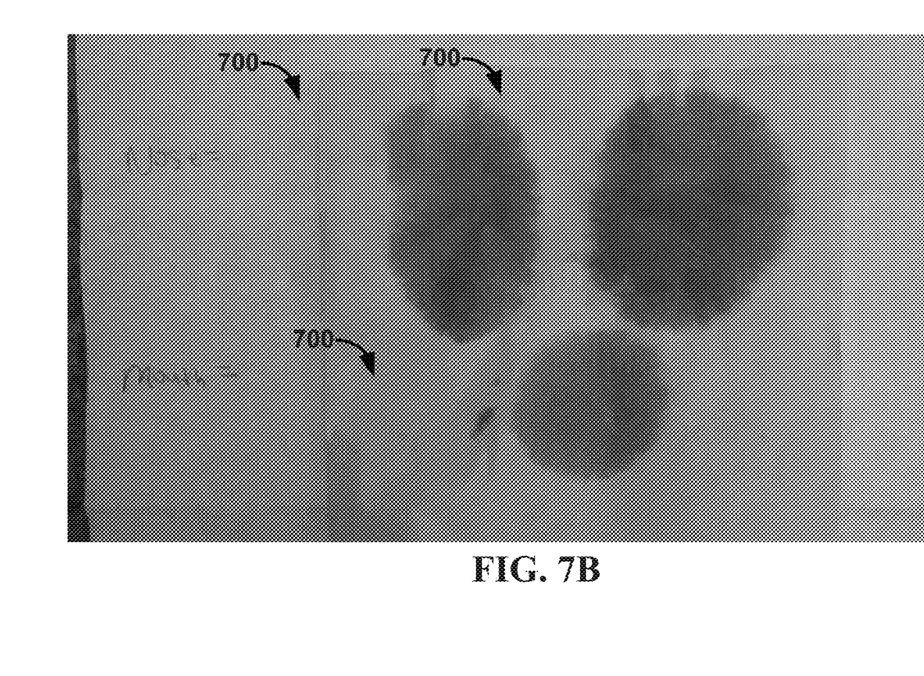
Figure 7C:
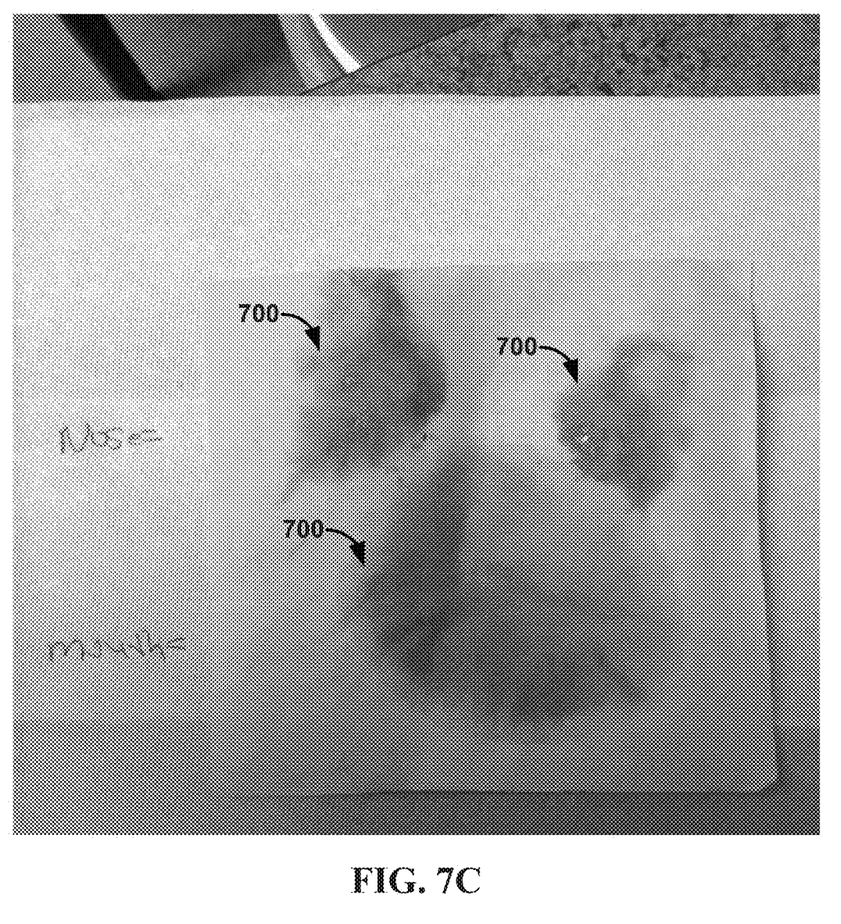

Color change to red/brown: FIGS. 7A-7C show that upon contact with the respiratory secretion, the tester paper changed from yellow to red and/or brown denoted by label 700. If the tester paper quickly developed into a deep red and/or brown color within 60 seconds, the subject was determined to have a bacterial infection. The subjects from this test group were then recommended to see a doctor for antibiotic treatment.

1.4 Conclusion

The results from this study show that tester paper of the present disclosure can serve as an efficient, at home, and user friendly tester for detecting a bacterial infection in a respiratory secretion. Specifically, within approximately 60 seconds, a subject can determine if they have a bacterial infection and/or are well based on the rapid change in color of the tester paper. Subjects additionally found the tester paper to be flexible and easily conformable with their nose and/or mouth area as well as to have a soft, non-irritating texture upon contact with their face.

I claim:

1. A method of determining whether a subject has a bacterial infection, the method comprising
   (1) providing a paper having a portion comprising turmeric to the subject, wherein the paper has a caliper of about 3 to about 6 (1 ply, mil), and one or more of:
   (a) a basis weight of about 20 to about 30 on a #500 scale;
   (b) an average tensile strength of about 10 to about 20 #/in;
   (c) a porosity of about 2 to about 4 (8 ply, 100 cc, sec.);
   (d) a moisture content of about 2% to about 10% by weight of the total paper;
   (e) a brightness of about 70% to about 90%; and/or
   (f) a stretch of about 1% to about 5% of the total dimensions of the paper, and
   (2) contacting the paper having the portion comprising turmeric with a respiratory secretion sample from the subject, wherein the paper having the portion comprising turmeric changes from a first color to a second color when contacted with the respiratory secretion sample if the subject has the bacterial infection.

2. The method of claim 1, wherein the average tensile strength is an average of a machine direction and cross direction tensile strength.

3. The method of claim 2, wherein the machine direction tensile strength is about 10 to about 15 #/in.

4. The method of claim 2, wherein the cross direction tensile strength is about 2 to about 5 #/in.

5. The method of claim 1, wherein the paper has a wet tensile strength of about 1 to about 4 #/in.

6. The method of claim 1, wherein the portion comprising turmeric changes from a first color to a second color within about 60 seconds after contact with the respiratory secretion sample.

7. The method of claim 1, wherein the paper is filter paper.

8. The method of claim 1, wherein the first color is a yellow hue.

9. The method of claim 1, wherein the second color is a red hue.

\* \* \* \* \*